United States Patent [19]

Hirose et al.

[11] Patent Number: 5,252,761
[45] Date of Patent: Oct. 12, 1993

[54] SILICONE-DISSOLVING AND SOLUBILIZING AGENTS

[75] Inventors: Tadashiro Hirose; Yoshihiro Ueda, both of Yokohama; Yoshiaki Takagi, Kanagawa, all of Japan

[73] Assignee: The Nisshin Oil Mills, Ltd., Tokyo, Japan

[21] Appl. No.: 634,527

[22] Filed: Dec. 27, 1990

[30] Foreign Application Priority Data

Jan. 10, 1990 [JP] Japan .................................. 2-4249

[51] Int. Cl.$^5$ .............................................. C07F 7/02
[52] U.S. Cl. ....................................... 554/77; 556/437
[58] Field of Search .................... 260/414; 556/437; 514/770, 772, 785; 554/77

[56] References Cited

U.S. PATENT DOCUMENTS

| | | | |
|---|---|---|---|
| 3,185,627 | 5/1965 | Kass | 167/90 |
| 3,393,040 | 7/1968 | Kass | 514/772 |
| 5,008,100 | 4/1991 | Zecchino et al. | 514/847 |

FOREIGN PATENT DOCUMENTS 766736 1/1957 United Kingdom .
8400884 3/1984 World Int. Prop. O. .

OTHER PUBLICATIONS

Jellinek, Cosmetics & Toiletrees, vol. 93, 1978, pp. 69–70, 72.

*Primary Examiner*—José G. Dees
*Assistant Examiner*—Deborah D. Carr
*Attorney, Agent, or Firm*—Bacon & Thomas

[57] ABSTRACT

A branched monoester represented by the formula $R^1COOR^2$ acts as a silicone-dissolving or solubilizing agent. In the formula, $R^1$ is an isoalkyl group having 4 to 17 carbon atoms, and $R^2$ is an isoalkyl group having 3 to 18 carbon atoms.

13 Claims, No Drawings

SILICONE-DISSOLVING AND SOLUBILIZING AGENTS

BACKGROUND OF THE INVENTION

1. Field of the Invention

The present invention relates to silicone-dissolving and solubilizing agents.

2. Description of the Related Art

Silicones are widely used in various fields, including industries, cosmetics and foodstuffs, and various kinds of silicones are on the market. For example, silicones are used as a water repelling agent, n anti-foaming agent, a mold release agent, and contained as an additive in a cosmetic article and a paint. Also, silicones are used as a lubricant. Various kinds of silicones are known to the art including, for example, general silicones such as dimethyl polysiloxane, methyl phenyl polysiloxane, and methyl hydrogen polysiloxane; various kinds of modified silicones; and copolymer type silicones. The types of silicones are also being diversified in accordance with expansion of the field of use of the silicones. Further, dependent on the use, silicones having a very wide range of viscosity have been developed. In fact, some of the silicones have such a low viscosity as only several centistokes (cs), and other silicones have such a high viscosity as about one million centistokes. The solubility of the silicone in another oily material is dependent greatly on the viscosity of the silicone, which is increased with increase in the degree of polymerization of the silicone.

In general, silicones are low in solubility in various kinds of oily materials. For example, silicones are insoluble in mineral oils, animal and vegetable oils, and almost all the synthetic esters, particularly, synthetic esters represented by fatty acid esters used in cosmetics. It is known that silicones have a solubility in some substances including isopropyl palmitate and isopropyl myristate as well as isoparaffin and cyclic silicones. However, isopropyl palmitate and isopropyl myristate leaves problems in terms of irritant action and stability. On the other hand, isoparaffin is accompanied by odor which is considered to be derived from the degree of refining. Further, the cyclic silicone is not satisfactory in terms of safety.

Under the circumstances, it is of high concern to develop a agent for dissolving silicones without bringing about the above-noted difficulties inherent in the prior art. It is also of high concern to develop a solubilizing agent for making silicones soluble in an oily material which can hardly dissolve the silicones.

SUMMARY OF THE INVENTION

An object of the present invention is to provide a silicone-dissolving or solubilizing agent which dissolves or solubilizes silicones, having a high compatibility with silicones, low in its irritating action to the skin, and excellent in stability and safety.

According to the present invention, there is provided a silicone-dissolving or solubilizing agent comprising at least one branched monoester represented by the general formula (I):

$$R^1 COOR^2 \quad (I)$$

where $R^1$ is an isoalkyl group having 4 to 17 carbon atoms, and $R^2$ is an isoalkyl group having 3 to 18 carbon atoms.

A method for dissolving or solubilizing silicones using the monoester of the invention, as well as a solution of a silicone dissolved in the monoester of the invention, are also within the scope of the present invention.

DETAILED DESCRIPTION OF THE PREFERRED EMBODIMENTS

The monoester of the present invention represented by the formula (I) can be produced by the reaction of a branched aliphatic carboxylic acid represented by the formula (II):

$$R^1 COOH \quad (II)$$

where $R^1$ is an isoalkyl group having 4 to 17 carbon atoms, with a branched aliphatic alcohol represented by the formula (III):

$$R^2 OH \quad (III)$$

where $R^2$ is an isoalkyl group having 3 to 18 carbon atoms.

The aliphatic carboxylic acids represented by formula (II) include branched carboxylic acids having a total of 5 to 18 carbon atoms, such as isopentanoic acid, isohexanoic acid, isoheptanoic acid, isooctanoic acid, isononanoic acid, isodecanoic acid, isotridecanoic acid, isomyristic acid, isopalmitic acid, and isostearic acid.

The aliphatic alcohols used in the present invention include, for example, isopropyl alcohol, isobutyl alcohol, isopentyl alcohol, isohexyl alcohol, isoheptyl alcohol, isooctyl alcohol, isononyl alcohol, isodecyl alcohol, isotridecyl alcohol, isomyristyl alcohol, isopalmityl alcohol and isostearyl alcohol.

It should be noted that the monoester represented by the formula (I) is an ester between the carboxylic acid represented by the formula (II) and the alcohol represented by the formula (III). It follows that "$R^1$" in the formula (I) can be defined as an alkyl residue of the $C_5$ to $C_{18}$ carboxylic acid represented by the formula (II). Likewise, "$R^2$" in the formula (I) can be defined as an alkyl residue of the $C_3$ to $C_{18}$ alcohol represented by the formula (III). Preferably, $R^1$ has 7 to 17 carbon atoms, and $R^2$ has 8 to 18 carbon atoms.

The esterification reaction can be carried out according to the known method under the atmospheric or reduced pressure in the presence or absence of a catalyst such as sulfuric acid or zinc oxide, with the acid and alcohol reactants used at a mole ratio of about 1:1. The reaction temperature is usually about 150° to 200° C., and the reaction time is usually about 10 to 20 hours. The esterification reaction can be conveniently carried out in a solvent such as xylene or toluene.

After the esterification reaction, the reaction product can be subjected to post-treatments by the known method, if desired. For example, the reaction mixture may be decolored with a decoloring agent, may be refined for deodoring the synthesized ester or may be subjected to vacuum distillation for the refining purpose.

The esters of the present invention are colorless and odorless, and are liquid at room temperature. They have excellent oxidative stability, and high resistances to acidic or alkaline hydrolysis. Further, they are not irritant. In addition to these basic properties, the esters of the present invention exhibit an excellent compatibility with silicones. To be more specific, the esters of the present invention can dissolve various silicones having a viscosity ranging from only several centistokes up to about one million centistokes including, for example, general-purpose silicones such as dimethylpolysiloxane, methylphenylpolysiloxane, and methylhydrogenpolysiloxane; variously modified silicones; and copolymer type silicones. The silicones can be dissolved to form a solution, if the silicones are simply mixed with the esters of the present invention at room temperature. Specifically, silicones are almost freely miscible with the esters of the invention to form a solution. The resultant solution can form a solution with a silicone-insoluble oil material such as liquid paraffin, squalane, various fatty acid triglycerides including glyceryl triisooctanoate, and mixed triglyerides of caprylic acid and capric acid, or a mixture thereof, in an amount of the silicone-insoluble oil material of 4 to 50 parts by weight based on 100 parts by weight of said resultant solution. In other words, the esters of the present invention can solubilize a silicone in a silicone-insoluble oil. In preparing silicone-containing formulations, it is convenient to dissolve a silicone in the ester of the invention, together with a silicone-insoluble oil, if necessary, to form a solution, and then to mix the resultant solution with the other components of the formulations.

The silicone-dissolving or solubilizing agent, i.e., ester, of the present invention can be applied to various articles. For example, the agent can be applied to cosmetics. In this case, various cosmetics can be prepared by adding working components and optional components, as desired, to the ester of the present invention. To be more specific, the cosmetics can be prepared by the ordinary method, in which the ester of the present invention is substituted for all or part of the oil component, emollient agent, etc. used in the various cosmetics containing the conventional silicone. The amount of the ester of the present invention may vary in a wide range, but the ester is usually used in cosmetics in an amount of 0.1 to 30% by weight. The kinds of the cosmetics are not particularly restricted. Specifically, the ester of the invention can be applied to cosmetics for the hair, cosmetics for the hair washing, cosmetic solutions, creamy emulsions, packs, foundations, puffs, lip sticks, facial cosmetics, nail cosmetics, cosmetics for bath, cosmetic oils, face-washing agents, and soaps. Further, the ester of the invention can be applied to various silicone-containing household articles and parts of vehicles in addition to the cosmetic articles exemplified above.

The ester of the invention is superior to the conventional silicone-dissolving agent in the silicone-dissolving and solubilizing capability. Thus, the ester permits moderating the restriction in the silicone content of an article utilizing a silicone and also permits widening the field of us of a silicone. In addition, the ester of the invention, which dissolves or solubilizes silicones, serves to stabilize the silicone-containing system, with the result that the silicone is enabled to exhibit its inherent, excellent function sufficiently. Further, the ester of the invention is less irritant and is excellent in safety and stability, and thus permits producing an article of a high reliability. Still further, the ester of the present invention can be used for removing a silicone-containing article applied on surfaces. For example, the ester can be used in a cleansing cream, a hair treatment agent, etc., when it comes to the cosmetics, and can be used for removing an oil film when it comes to parts of vehicles.

EXAMPLE 1

Preparation of Isooctyl Isononanoate

Into a 500 ml three-necked flask provided with a stirrer, a thermometer, a nitrogen gas blowing pipe, and a water separation pipe, 160 g of isononanoic acid, and 130 g of isooctyl alcohol were charged, together with 0.3% based on the sum of the acid and the alcohol of a stannous chloride powder as a catalyst, and 5% based on the sum of the acid and the alcohol of xylol as a reflux solvent. The reaction mixture was allowed to react at 150° to 200° C. for 10 hours while being stirred. After the reaction, the reaction product was decolored with activated clay, followed by deodoring the product by the ordinary method, obtaining 153 g of the desired ester.

EXAMPLE 2

Preparation of Isononyl Isomyristate

A reaction between 200 g of isomyristic acid and 130 g of isononyl alcohol was carried out as in Example 1, obtaining 118 g of the desired ester.

EXAMPLE 3

Preparation of Isodecyl Isononanoate

A reaction between 160 g of isononanoic acid and 160 g of isodecyl alcohol was carried out as in Example 1, obtaining 141 g of the desired ester.

Table 1 shows the solubility of silicones (dimethyl polysiloxanes) in each of the esters prepared in Examples 1 to 3, together with the solubility of of the silicones in the other oily materials. As apparent from Table 1 the ester of the present invention exhibits an excellent solubility for silicones having a viscosity ranging from low to high.

Table 2 shows the solubility of a silicone-insoluble oily material in a mixture of the ester, i.e., each of the esters prepared in Examples 1 to 3 or another silicone-solubilizing ester (isopropyl myristate) with a silicone (dimethyl polysiloxane). The values given in Table 2 denote the percentage of the silicone-insoluble oil which was dissolved in the silicone-ester 1:1 mixture (weight basis). As apparent from Table 2, the ester of the present invention exhibits an excellent solubilizing capability to making silicones soluble in a silicone-insoluble oil.

Table 3 shows the data covering the case where the ester obtained in Example 3 was added to a wax containing silicone. To be more specific, 35 parts by weight of the ester obtained in Example 3 was mixed with 25 parts by weight of a silicone having a viscosity of 100 cs. The mixture was added to 40 parts by weight of a molten paraffin wax. After solidification, the sample thus prepared was allowed to stand on a filter paper at room temperature. Under this condition, the degree of silicone separation was examined by measuring the change with time in the weight of the sample. For comparison, another sample was prepared as above, except that the ester obtained in Example 3 was replaced by liquid paraffin, for examining the degree of silicone separation.

As apparent from Table 3, the ester of the present invention makes the silicone soluble in wax and effectively suppresses the silicone separation.

EXAMPLE 4

Safety Test of Esters

The primary irritation of the ester to the human body was examined by a closed patch test. Specifically, the stratum corneum and sebum of the skin in the front part or arm portion of a human body were removed. Then, a lint cloth (1 inch×1 inch) was coated with an ester sample and put on the skin surface. Under this condition, the lint cloth was covered with an oil-impregnated paper, which was further fixed at the four corners with an adhesive plaster, and held by a bandage. The test was applied to 20 healthy persons, and the irritant action was determined 24 hours, 48 hours, and one week after the ester application. The irritant action was not recognized at all in the case of the ester prepared in any of Examples 1 to 3.

Further, an odor emission test of the ester was conducted as follows. Specifically, about 0.2 g of an ester sample was applied to a body front portion (2 inches×2 inches), and the odor emission was determined 10 minutes, 20 minutes, 30 minutes, 1 hour, 4 hours and 8 hours after the ester sample application. The test was performed on 20 healthy persons. The odor emission was not recognized at all in the case of the ester prepared in any of Examples 1 to 3.

EXAMPLE 5

Stability Test of Ester

Into a 250 ml a sample bottle, 100 ml of the ester prepared in each of Examples 1 to 3, and 100 ml of a standard buffer solution (prepared by Wako Junyaku Kogyo K.K., Japan) having a pH value of 4 or 9 were charged. Then, a nitrogen gas was sealed in the sample bottle, and the bottle was left in a constant temperature bath maintained at 55° C. A change with time in the properties of the ester was measured by separating the oil layer after the bottle was left to stand in the constant temperature bath and measuring the acid value of the oil layer. Table 4 shows the results.

EXAMPLE 6

Silicone-Containing Compositions

| (1) | Aerosol Hair Conditioner | |
|---|---|---|
| | Ester of Example 1 | 1.5% by weight |
| | Propylene glycol | 0.2% by weight |
| | Methyl phenyl polysiloxane | 0.1% by weight |
| | Perfume | 0.2% by weight |
| | Modified alcohol (anhydrous) | 18.0% by weight |
| | Propellant | 80.0% by weight |
| (2) | Emollient Lotion | |
| | Microcrystalline wax | 1.0% by weight |
| | Dimethyl polysiloxane | 2.0% by weight |
| | Beeswax | 2.0% by weight |
| | Ester of Example 2 | 30.0% by weight |
| | Sorbitan sesquioleic acid ester | 4.0% by weight |
| | Polyoxyethylene sorbitan monooleic acid ester (20 E.O) | 1.0% by weight |
| | Aluminum stearate | 0.2% by weight |
| | Glycerin | 8.0% by weight |
| | Anticorrosion agent, anti-oxidizing agent, perfume | as required |
| | Refined water | balance |
| (3) | Foundation (oily ointment) | |
| | Ester of Example 2 | 24.0% by weight |
| | Isopropyl palmitate | 15.0% by weight |
| | Lanolin alcohol | 2.0% by weight |
| | Dimethyl polysiloxane | 5.0% by weight |
| | Microcrystalline wax | 5.0% by weight |
| | Candelilla wax | 1.0% by weight |
| | Ozokerite | 8.0% by weight |
| | Titanium oxide | 15.0% by weight |
| | Kaolin | 15.0% by weight |
| | Talc | 6.0% by weight |
| | Coloring pigment | 4.0% by weight |
| | Anticorrosion agent, anti-oxidizing agent, perfume | as required |
| (4) | Foundation (cake type) | |
| | Ester of Example 3 | 10.0% by weight |
| | Sorbitan sesquioleate | 3.5% by weight |
| | Dimethyl polysiloxane | 3.0% by weight |
| | Titanium oxide | 10.0% by weight |
| | Colloidal kaolin | 25.0% by weight |
| | Talc | 45.1% by weight |
| | Red oxide | 0.8% by weight |
| | Yellow iron oxide | 2.5% by weight |
| | Black iron oxide | 0.1% by weight |
| | Anticorrosion agent, perfume | as required |
| (5) | Lip Stick | |
| | Candelilla wax | 10.0% by weight |
| | Carnauba wax | 4.0% by weight |
| | Ceresin | 3.0% by weight |
| | Microcrystalline wax | 3.0% by weight |
| | Dimethyl polysiloxane | 10.0% by weight |
| | Glycerin tri-2-ethylene hexanoate | 40.0% by weight |
| | Diisostearyl malate | 20.0% by weight |
| | Red 202 | as required |
| | Red 226 | as required |

TABLE 1

(Dimethyl polysiloxane: Oil agent = 1:1 by weight)

| | Viscosity (Cs) of dimethyl polysiloxane | | | | | | |
|---|---|---|---|---|---|---|---|
| Oil Agent | 100 | 1,000 | 3,000 | 10,000 | 60,000 | 100,000 | 1,000,000 |
| Example 1 | ○ | ○ | ○ | ○ | ○ | ○ | ○ |
| Example 2 | ○ | ○ | ○ | ○ | ○ | ○ | ○ |
| Example 3 | ○ | ○ | ○ | ○ | ○ | ○ | ○ |
| Isoporpyl palmitate | ○ | Δ | Δ | Δ | Δ | Δ | Δ |
| Isopropyl myristate | ○ | ○ | Δ | Δ | Δ | Δ | Δ |
| Liquid paraffin | X | X | X | X | X | X | X |
| Squalane | X | X | X | X | X | X | X |
| Glyceryl triisooctylate | ○ | X | X | X | X | X | X |

○ ... mutually soluble;
Δ ... poor in mutual solubility;
X ... not mutually soluble

TABLE 2

(Dimethyl polysiloxane (3000 cs): Ester 1:1 by weight)

| Ester | Silicone-insoluble oil | | |
|---|---|---|---|
| | Liquid paraffin | Glyceryl triisooctylate | Iso-octyl p-methoxy cinnamate |
| Example 1 | 35% | 20% | 5% |
| Example 2 | 40 | 20 | 5 |
| Example 3 | 50 | 30 | 10 |
| Isopropyl myristate | 30 | 10 | 0 |

TABLE 3

(Degree (%) of silicone separation from wax)

| | Sample of present invention | Use of liquid paraffin |
|---|---|---|
| Starting time | 0.00 | 0.00 |
| 3 days later | 0.06 | 3.71 |
| 7 days later | 0.14 | 6.40 |

TABLE 4

| Sample | pH of buffer solution | Start time | 1 day | 4 days | 1 week | 1 month | 3 months |
|---|---|---|---|---|---|---|---|
| Example 1 | 4 | 0.2 | 0.2 | 0.2 | 0.2 | 0.3 | 0.5 |
| | 9 | 0.2 | 0.2 | 0.2 | 0.2 | 0.4 | 1.1 |
| Example 2 | 4 | 0.1 | 0.1 | 0.1 | 0.1 | 0.1 | 0.1 |
| | 9 | 0.1 | 0.1 | 0.1 | 0.1 | 0.1 | 0.2 |
| Example 3 | 4 | 0.1 | 0.1 | 0.1 | 0.1 | 0.2 | 0.4 |
| | 9 | 0.1 | 0.1 | 0.1 | 0.2 | 0.3 | 0.9 |
| Isopropyl myristate | 4 | 0.2 | 0.2 | 0.2 | 0.2 | 0.5 | 1.3 |
| | 9 | 0.2 | 0.2 | 0.3 | 0.4 | 0.7 | 2.2 |

What is claimed is:

1. A solution comprising:

at least one branched monoester represented by the general formula:

$$R^1OOR^2 \tag{I}$$

where $R^1$ is an isoalkyl group having 4 to 17 carbon atoms, and $R^2$ is an isoalkyl group having 3 to 18 carbon atoms; and a linear silicone having a viscosity of 100 centistokes or more dissolved in said monoester.

2. The solution according to claim 1, wherein $R^1$ has 7 to 17 carbon atoms.

3. The solution according to claim 1, wherein $R^2$ has 8 to 18 carbon atoms.

4. The solution according to claim 1, wherein said monoester is selected from isooctyl isononanoate, isononyl isomyristate, and isodecyl isononanoate.

5. A solution according to claim 1, wherein the silicone has a viscosity of 1000 centistokes or more.

6. A solution according to claim 5, wherein the silicone has a viscosity of 3000 centistokes or more.

7. A solution comprising:

at least one branched monoester represented by the general formula:

$$R^1COOR^2 \tag{I}$$

where $R^1$ is an isoalkyl group having 4 to 17 carbon atoms, and $R^2$ is an isoalkyl group having 3 to 18 carbon atoms; and a linear silicone having a viscosity of 100 centistokes or more dissolved therein; and a silicone-insoluble oil dissolved therein.

8. The solution according to claim 7, wherein $R^1$ has 7 to 17 carbon atoms.

9. The solution according to claim 7, wherein $R^2$ has 8 to 18 carbon atoms.

10. The solution according to claim 7, wherein said monoester is selected from isooctyl isononanoate, isononyl isomyristate, and isodecyl isononanoate.

11. The solution according to claim 7, which contains 5 to 50 parts by weight of said silicone insoluble oil based on 100 parts by weight of the solution of said silicone dissolved in said monoester.

12. A solution according to claim 7 wherein the silicon has a viscosity of 1000 centistokes or more.

13. A solution according to claim 12 wherein the silicon has a viscosity of 3000 centistokes or more.

* * * * *